United States Patent [19]

Ichijima et al.

[11] Patent Number: 4,522,917
[45] Date of Patent: Jun. 11, 1985

[54] PHOTOGRAPHIC SILVER HALIDE LIGHT-SENSITIVE MATERIAL

[75] Inventors: Seiji Ichijima; Keiji Mihayashi; Isamu Itoh, all of Kanagawa, Japan

[73] Assignee: Fuji Photo Film Co., Ltd., Kanagawa, Japan

[21] Appl. No.: 553,262

[22] Filed: Nov. 18, 1983

[30] Foreign Application Priority Data

Nov. 19, 1982 [JP] Japan ................................ 57-203446

[51] Int. Cl.$^3$ ......................... G03C 1/46; G03C 1/02
[52] U.S. Cl. .................................... 430/564; 430/505; 430/566; 430/955; 430/957; 430/959; 430/960; 430/546; 430/607; 430/613
[58] Field of Search ................................ 430/955–960, 430/223, 566, 505, 546, 607, 613

[56] References Cited

U.S. PATENT DOCUMENTS 3,396,127  8/1968  Burness et al. .................... 430/621
4,254,217  3/1981  Ohashi et al. ...................... 430/623
4,363,865  12/1982  Reczek et al. ...................... 430/223

FOREIGN PATENT DOCUMENTS 2626315  12/1976  Fed. Rep. of Germany .
179842  11/1982  Japan .

Primary Examiner—Mary F. Downey
Attorney, Agent, or Firm—Sughrue, Mion, Zinn, Macpeak & Seas

[57] ABSTRACT

A photographic silver halide light-sensitive material is disclosed. The material is comprised of a support and a photographic layer or layers on the support. The photographic layer contains at least one of the compounds represented by the general formula: A—OCH$_2$—Z (wherein A is a group capable of undergoing cleavage on application of alkali hydrolysis, and Z is a photographically useful group containing a nitrogen atom through which it is linked to the group A—OCH$_2$—). The compounds, i.e., photographically useful group precursors, as used herein are stable during the storage of the raw film and can release the photographically useful group at a controlled speed during development.

16 Claims, No Drawings

PHOTOGRAPHIC SILVER HALIDE LIGHT-SENSITIVE MATERIAL

FIELD OF THE INVENTION

The present invention relates to a photographic light-sensitive material and, more particularly, to a photographic silver halide light-sensitive material containing a precursor of a photographically useful group.

BACKGROUND OF THE INVENTION

In general, a photographic silver halide light-sensitive material (hereinafter sometimes referred to merely as a "light-sensitive material"), when exposed imagewise and then developed, provides an image or image pattern. In some cases, an antifoggant, a development inhibitor, etc., are added in combination with a development agent to a processing solution for the purpose of improving image quality, and a development accelerator, a sensitizer, etc., are added for the purpose of increasing sensitivity. These additives are called herein "photographically useful compounds".

When such photographically useful compounds are incorporated in a light-sensitive material or film, they seriously reduce sensitivity during the storage of the film, increasing the formation of fog, because they coexist with silver halide. This problem could be overcome if they are controlled to exhibit their activity just at the stage of development. It has, therefore, been considered to use their precursors which are prevented from reacting with silver halide during the storage of the film or at the stage of exposure, but which are decomposable with alkalis so as to release a photographically useful group timely at the stage of development. One of the features of such precursors is that they are prevented from reacting prior to the processing, and another feature is that the timing of releasing a necessary compound at the stage of development can be controlled.

In general, an alkaline solution is used as a developing solution. Therefore, it has been attempted to meet both the requirements, i.e., the proper releasing speed of the photographically useful group at the stage of development and the stability of the raw film during the storage thereof, by utilizing the difference in hydroxy ion concentration between during the storage of the raw film and at the stage of development. However, since the difference in hydroxy ion concentration is not so large for commonly used developers (pH: 8–13), it is difficult to meet both the requirements particularly when the photographically useful group is desired to be released just after the start of development as in the case of a sensitizer, for example.

Various compounds have been developed to solve the above-described problem, including those compounds as described in U.S. Pat. Nos. 4,209,580, 3,241,967 and 4,310,612. These compounds, however, are not satisfactory and must be further improved. They exhibit the necessary photographic performance to a certain extent when used in a light-sensitive material which is to be processed with a processing solution having a pH as high as 13 or more. Even in this case, the storage stability can be ensured only by sacrificing the releasing speed of the photographically useful group at the stage of development.

SUMMARY OF THE INVENTION

An object of the invention is to provide a light-sensitive material containing a precursor of a photographically useful group, in which both the stability of the precursor during the storage of the material and the proper releasing speed of the photographically useful group at the stage of development are satisfied.

The present invention relates to a photographic silver halide light-sensitive material containing in a photographic constitutive layer on a support at least one compound represented by the general formula (I):

A—OCH$_2$—Z  (I)

wherein A is a group capable of undergoing cleavage by alkali hydrolysis, and Z is a photographically useful group containing a nitrogen atom through which it is linked to the group: A—OCH$_2$—.

DETAILED DESCRIPTION OF THE INVENTION

Photographically useful group precursors as used in the light-sensitive material of the invention are not only stable during the storage of the raw film, but can release the photographically useful group at a controlled speed when the light-sensitive material is developed.

The precursors of the invention are represented by the general formula (I):

A—OCH$_2$—Z  (I)

wherein A is a group capable of undergoing cleavage by alkali hydrolysis, and Z is a photographically useful group containing a nitrogen atom through which it is linked to the group A—OCH$_2$—.

The precursor represented by the general formula (I) releases the photographically useful group, Z, according to the following reaction scheme:

First Stage

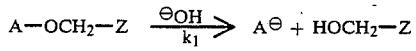

$$A-OCH_2-Z \xrightarrow{\ominus OH}{k_1} A^\ominus + HOCH_2-Z$$

Second Stage

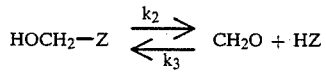

$$HOCH_2-Z \underset{k_3}{\overset{k_2}{\rightleftarrows}} CH_2O + HZ$$

where k$_1$, k$_2$ and k$_3$ represent rate constants of reaction for the respective reactions.

It is known, as described in *Bull. Soc. Chim. France*, 138 (1955), that for the equilibrium reaction at the second stage, the rate of formation of a methylol body (k$_3$) is greater than the rate of decomposition of the methylol body (k$_2$). The formation and decomposition of methylol benzamide are described in detail in the foregoing reference. Moreover, in the equilibrium reaction at the second stage, the reaction of decomposition of the methylol body is a first-order reaction, whereas the reaction of formation of the methylol body is a second-order reaction. In the first-order reaction, the yield of the desired product does not depend on the concentration of starting material. In the second-order reaction, however, the yield of the desired product is dependent on the concentration of the starting material. That is, in the second-order reaction, the conversion at a certain time is higher at high concentrations than at low concentrations.

Therefore, when predetermined values of $k_2$ and $k_3$ are given for the equilibrium reaction at the second stage, the concentration ratio of the methylol body to $Z^\ominus$ varies with changes in concentration. This discussion is based on the fundamental theory of reaction rate.

The precursor of the invention is usually dissolved in a high boiling oil and dispersed in gelatin, for example, and incorporated in the film. This procedure is the same as that as used in coating a coupler on a film in the preparation of a color photographic light-sensitive material. It is considered, therefore, that during the storage of the raw film, the precursor is present in oil droplets in a high concentration, and even if the precursor decomposes slightly with the lapse of time, the concentration of the methylol body is maintained at a high level in the equilibrium reaction at the second stage and hence the amount of $Z^\ominus$ being released as the photographically useful group is very small. It is believed based on the reasons as described above that the precursor of the invention is superior in stability during the storage of the raw film and does not exert adverse influences such as desensitization and fog.

During development, a developer diffuses in the film, swelling the film and allowing the precursor to diffuse out of the oil droplets. As a result, the concentration of the precursor drops, the precursor is hydrolyzed (the reaction at the first stage), and then the decomposition reaction of the methylol body occurs, releasing a sufficient amount of a photographically useful group.

It is believed based on the reasons as described above that when the precursor of the invention is incorporated in the film, it sufficiently exhibits a photographic action during development and, moreover, its stability is good during the storage of the raw film.

The speed at which the photographically useful group is released varies, of course, with the properties of the atomic group represented by A. Thus, the present invention provides a group of compounds in which the releasing speed of any type of photographically useful group at the stage of development can be adjusted to the necessary one in various light-sensitive materials.

As the photographically useful groups as used herein, photographic reagents conventionally used can be used in photographic materials according to conventional procedures for various purposes. For example, when the reagent is a development inhibitor, it can be used for the purpose of inhibiting the development of silver halide. When the reagent is an auxiliary developing agent, it can be used for the purpose of accelerating the development of silver halide. Moreover, when the reagent is a silver halide solvent, it can be used for the purpose of accelerating the dissolution of silver halide.

Although the optimum releasing speed of the photographically useful group varies with the purpose, it is generally useful that the rate constant of psuedo first-order hydrolysis in a buffer with a pH of 10 at 25° C. is within the range of from $1\times10$/second to $1\times10^{-6}$/second.

Examples of the hydrolyzable groups represented by A in the general formula (I) are shown below:

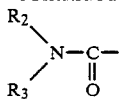

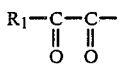

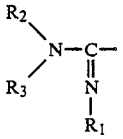

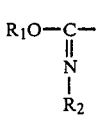

Of these groups, the following are particularly preferred.

and

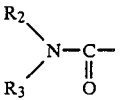

The symbols of the formulae as described above are as defined below:

$R_1$ is an aliphatic group containing from 1 to 22 carbon atoms, an aromatic group containing from 6 to 10 carbon atoms or a heterocyclic group; and $R_2$ and $R_3$ are each a hydrogen atom, an aliphatic group containing from 1 to 22 carbon atoms, an aromatic group containing from 6 to 10 carbon atoms, or a heterocyclic group. When $R_2$ and $R_3$ are contained simultaneously in one molecule, they may be the same or different. Moreover, $R_2$ and $R_3$ may combine together to form a ring.

The aliphatic group represented by $R_1$, $R_2$ and $R_3$ may be substituted or unsubstituted, chain-like or cyclic, or saturated or unsaturated. Preferred substituents for the aliphatic group include an alkoxy group, an aryloxy group, an acylamino group, a carbamoyl group, a halogen atom, a sulfonamido group, a sulfamoyl group, a carboxyl group, an alkanoyloxy group, a benzoyloxy group, a cyano group, a hydroxyl group, a ureido group, a carbonyl group, an aryl group, an alkylsulfonyl group, an alkoxycarbonyl group, an alkylureido group, an imidazolyl group, a furyl group, a nitro group, a phthalimido group, a thiazolyl group, an alkanesulfonamido group, an alkanesulfamoyl group, an arylcarbonyl group, an imido group, and an alkoxycarbonylamino group.

When $R_1$, $R_2$ and $R_3$ each represents an aromatic group (particularly a phenyl group), the aromatic group may be substituted. The aromatic group (e.g., a phenyl group) may be substituted by a halogen atom, a nitro group, a hydroxyl group, a cyano group, a carboxyl group, or an alkyl, alkenyl, alkoxy, alkoxycarbonyl, alkanoyloxy, alkoxycarbonylamino, aliphatic amido, alkylsulfamoyl, alkylsulfonamido, alkylureido, alkylsulfonyl or alkyl-substituted succinimido group containing 32 or less carbon atoms. In this case, the alkyl moiety of such substituents may contain an aromatic divalent group (e.g., phenylene) in the chain thereof. The phenyl group may be substituted by an aryloxy group, an aryloxycarbonyl group, an arylcarbamoyl group, an arylamido group, an arylsulfamoyl group, an arylsulfonamide group or an arylureido group. The aryl moiety of such substituents may be further substituted by one or more alkyl groups containing 1 to 22 carbon atoms in total.

When $R_1$, $R_2$ and $R_3$ each represents a heterocyclic group, the heterocyclic group is linked through one of the carbon atoms constituting the ring to a linking group with a photographically useful group bound thereto. Examples of such heterocyclic groups include thiophene, furan, pyran, pyrrole, pyrazol, pyridine, pyrazine, pyrimidine, pyridazine, indolizine, imidazole, thiazole, oxazole, triazine, thiadiazine, and oxazine. These groups may further contain a substituent or substituents on the ring thereof.

Of the photographically useful groups represented by Z in the general formula (I), those groups represented by the following general formulae (II), (III), (IV) and (V) are especially preferred.

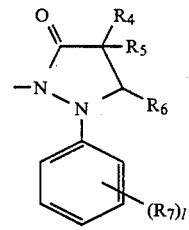
(II)

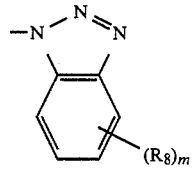
(III)

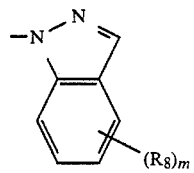
(IV)

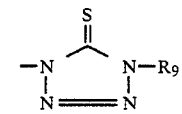
(V)

The symbols of the formulae as described above are as defined below:

$R_4$, $R_5$ and $R_6$ represent independently a hydrogen atom, an aliphatic group ($C_1$-$C_{22}$), or an aromatic group ($C_6$-$C_{10}$).

$R_7$ represents an amino group, an alkoxyl group ($C_1$-$C_{22}$), an aryloxy group ($C_6$-$C_{10}$), a hydroxyl group, an alkyl group ($C_1$-$C_{22}$), an aryl group ($C_6$-$C_{10}$), a halogen atom, a carbonamide group, a sulfonamide group, an alkanoyloxy group ($C_1$-$C_{22}$), a benzoyloxy group, a ureido group, a carbamate group, a carbamoyloxy group, a carbonate group or a carboxyl group.

$R_8$ represents the groups represented by $R_7$, an alkoxycarbonyl group ($C_1$-$C_{22}$), an aryloxycarbonyl group ($C_6$-$C_{10}$), a carbamoyl group, a sulfamoyl group, an alkanoyl group ($C_1$-$C_{22}$), a benzoyl group, an alkylsulfonyl group ($C_1$-$C_{22}$), an arylsulfonyl group ($C_6$-$C_{10}$), a cyano group, a sulfo group or a nitro group.

$R_9$ represents an aliphatic group ($C_1$-$C_{22}$) or an aromatic group ($C_6$-$C_{10}$).

$l$ represents 0 or an integer of from 1 to 5.

$m$ is 0 or an integer of from 1 to 4.

The foregoing substituents represented by $R_4$, $R_5$, $R_6$, $R_7$ and $R_8$ may further contain a substituent or substituents.

Typical examples of the precursors, of the formula A—OCH$_2$—Z, as used herein are shown below although the present invention is not limited thereto.

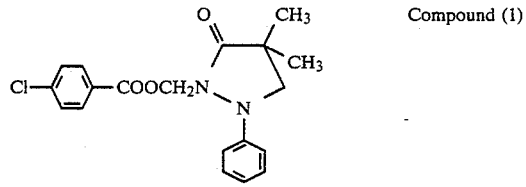
Compound (1)

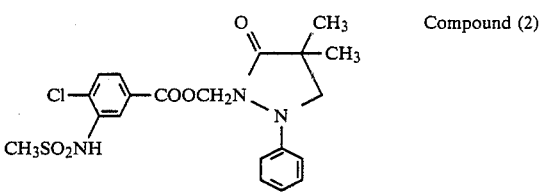
Compound (2)

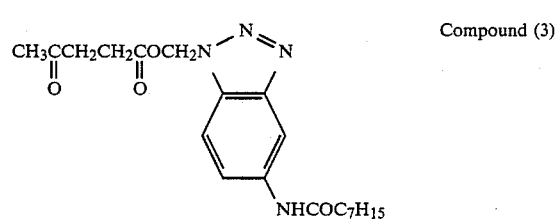
Compound (3)

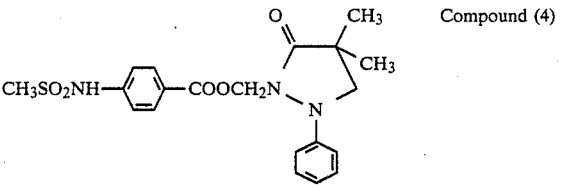
Compound (4)

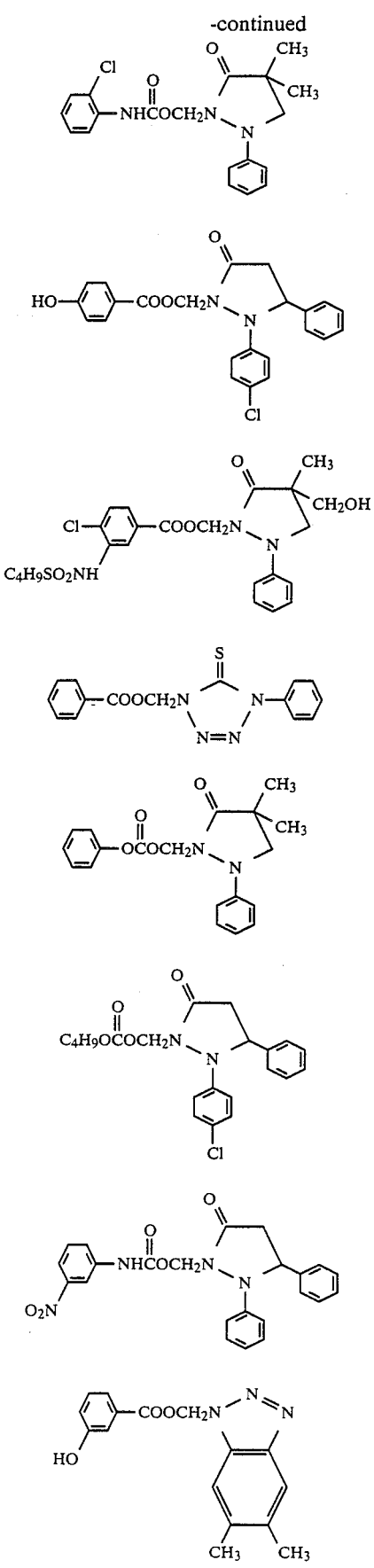
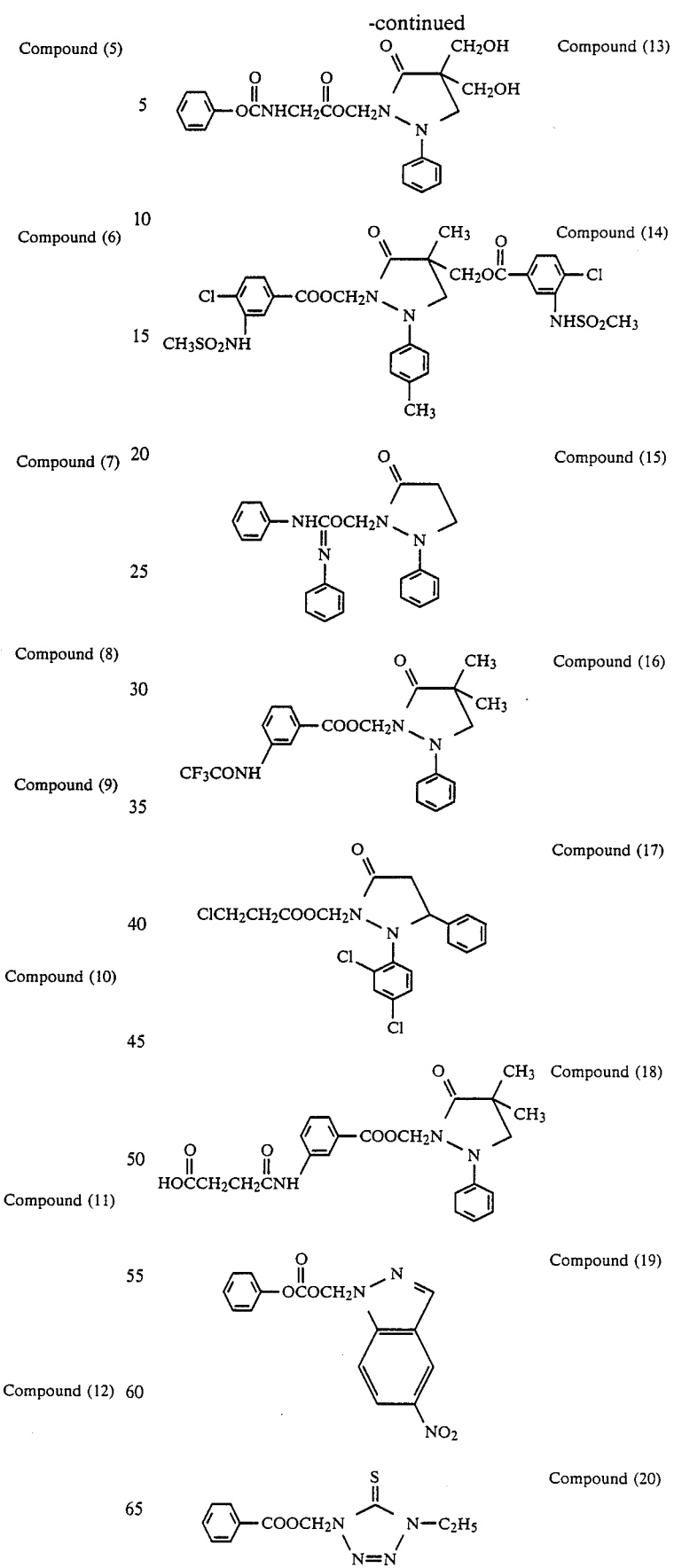

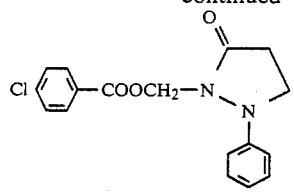
Compound (21)

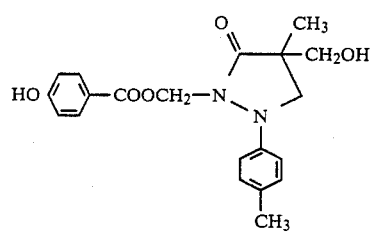
Compound (22)

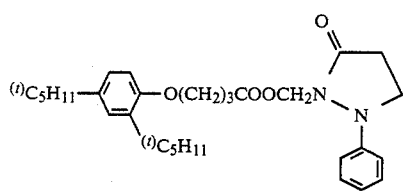
Compound (23)

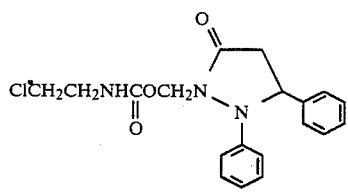
Compound (24)

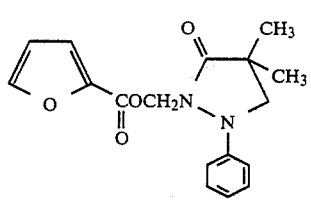
Compound (25)

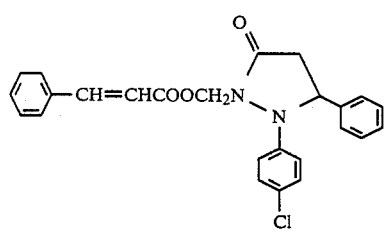
Compound (26)

The precursors of the invention can be synthesized according to the reaction formula as described below:

First Stage

Second Stage

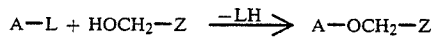

wherein A and Z are the same as defined above, and L is a halogen atom or a hydroxyl group.

When L represents a hydroxyl group at the second reaction stage, carbodiimide, for example, is used as a dehydrating-condensing agent. When L represents a halogen atom, a base may or may not be used as a deoxidizer.

Typical methods of preparation of the precursors of the invention are described below.

PREPARATION EXAMPLE 1

Synthesis of Compound (1)

First Stage:

4,4-Dimethyl-1-phenyl-3-pyrazolidone (152 g) was dissolved in 600 ml of acetic acid. To the solution as prepared above, 97 g of an aqueous solution containing 37% of formaldehyde was dropped with stirring at room temperature. The resultant mixture was stirred for 2 hours. At the end of the time, the solvent was distilled away under reduced pressure. To the residue thus obtained, 100 ml of toluene was added, and water was separated at the toluene azeotrope under reduced pressure. A mixture of 900 ml of hexane and 700 ml of ethyl acetate was added to the residue as obtained above which was then dissolved therein by heating. The resultant solution was allowed to cool to room temperature. Crystals precipitated were collected by filtration to obtain 120 g of 4,4-dimethyl-2-hydroxymethyl-1-phenyl-3-pyrazolidone.

Second Stage:

A mixture of 66 g of 4,4-dimethyl-2-hydroxy-methyl-1-phenyl-3-pyrazolidone as prepared above and 39 g of 4-chlorobenzoic acid was dissolved in 200 ml of N,N-dimethylformamide. To the solution thus prepared, 48 g of N-ethyl-N'(3-dimethylaminopropyl)carbodiimide hydrochloride was gradually added with stirring at room temperature. They were reacted at room temperature for 4 hours. At the end of time, the reaction mixture was poured into water and extracted with 1,000 ml of ethyl acetate. The organic layer was washed with water and then dried over anhydrous sodium sulfite. The solvent was distilled away under reduced pressure. The residue thus obtained was recrystallized from hexane and ethyl acetate to obtain 55 g of the desired Compound (1), m.p. 88°–89° C.

PREPARATION EXAMPLE 2

Synthesis of Compound (2)

4,4-Dimethyl-2-hydroxymethyl-1-phenyl-3-pyrazolidone (6.6 g) as obtained at the first stage in Preparation Example 1 and 7.2 g of 4-chloro-3-methanesulfonamidobenzoic acid were dissolved in 20 ml of N,N-dimethylformamide. To the solution thus prepared was dropped 2.6 g of N,N'-diisopropylcarbodiimide. They were reacted at room temperature for 1 hour. Then, solids (N,N'-diisopropyl urea) precipitated were filtered off, and the filtrate thus obtained was poured into water, followed by extracting with 200 ml of ethyl acetate. The organic layer was separated and washed with water. The ethyl acetate was distilled away under reduced pressure, and the residue was recrystallized from a mixed solvent of ethyl acetate and hexane to obtain 6.7 g of the desired Compound (2), m.p. 138°–140° C.

PREPARATION EXAMPLE 3

Synthesis of Compound (3)

1-Hydroxymethyl-5 (or 6)-octaneamidobenzotriazole (20 g) as prepared in the same manner as in the first stage of Preparation Example 1 and 8 g of 4-oxopentanoic acid were suspended in 100 ml of acetone. Additionally, 0.2 g of 4-dimethylaminopyridine was added thereto. A solution of 14.2 g of N,N'-dicyclohexylcarbodiimide dissolved in 10 ml of acetone was dropped to the solution as prepared above with stirring at room temperature. They were reacted at room temperature for 2 hours and moreover, at 50° C. for 2 hrs. The reaction mixture was allowed to cool to room temperature, and solids (N,N'-dicyclohexyl urea) precipitated were filtered off. The filtrate was condensed, and the residue thus obtained was crystallized from a mixed solvent of toluene and hexane to obtain 17 g of the desired Compound (3) in a waxy form.

PREPARATION EXAMPLE 4

Synthesis of Compound (4)

4,4'-Dimethyl-2-hydroxymethyl-1-phenyl-3-pyrazolidone (22 g) as prepared at the first stage of Preparation Example 1 and 22 g of 4-methanesulfonamidobenzoic acid were dissolved in a mixed solvent of 20 ml of dimethyl sulfoxide and 40 ml of N,N-dimethylformamide. Then, 0.3 g of 4-dimethylaminopyridine was added, and 13 g of N,N'-diisopropylcarbodiimide was dropped thereto. The resultant mixture was stirred for 4 hours. At the end of the time, 500 ml of ethyl acetate was added, and the mixture was washed with water. Crystals precipitated in the oil layer were filtered off, and the filtrate thus obtained was condensed under reduced pressure. The residue was recrystallized from ethyl acetate to obtain 29 g of the desired Compound (4), m.p. 153°–154° C.

PREPARATION EXAMPLE 5

Synthesis of Compound (5)

4,4'-Dimethyl-2-hydroxymethyl-3-pyrazolidone (13.2 g) as prepared in the first stage of Preparation Example 1 and 9.2 g of 2-chlorophenylisocyanate were dissolved in 40 ml of dimethyl sulfoxide. They were reacted at room temperature for 3 hours. At the end of the time, 100 ml of ethyl acetate was added, and the mixture was washed with water. The oil layer was separated and condensed under reduced pressure. The residue was recrystallized from a mixed solvent of ethyl acetate and hexane to obtain 8 g of the desired Compound (5), m.p. 119°–120° C.

PREPARATION EXAMPLE 6

Synthesis of Compound (9)

4,4'-Dimethyl-2-hydroxymethyl-3-pyrazolidone (3 g) as prepared in the first stage of Preparation Example 1 was suspended in 10 ml of ethyl acetate. Phenoxycarbonyl chloride (2 g) was dropped at 10° C. Additionally, 1.1 ml of pyridine was dropped at 10° C. At this temperature, they were stirred for 3 hours. The mixture was transferred to a dropping funnel and then washed with water. The oil layer was separated and dried over anhydrous sodium sulfate, and then the solvent was distilled away under reduced pressure. The residue was passed through a chromatographic column filled with 250 g of silica gel and using an eluting solution comprising a 2:1 mixture of hexane and ethyl acetate. A fraction containing the desired product was condensed to obtain 3.5 g of the desired Compound (9), m.p. 98°–101° C.

The compounds of the invention can be used in, for example, color photographic light-sensitive materials of the coupler system.

A method generally employed to form a color image using color photographic light-sensitive materials comprises developing the color photographic light-sensitive materials with aromatic primary amine developing agents in the presence of color couplers capable of forming dye on reacting with an oxidation product of the developing agent to obtain azomethine or indoaniline dye. The principle of the color developing method as described above was invented by L. D. Mannes and L. Godowsky in 1935, and various improvements have been made to develop the method presently employed in all parts of the world. In accordance with this system, color reproduction is usually conducted using the subtractive color process; i.e., silver halide emulsions sensitive selectively to blue, green and red, and color image-forming agents of yellow, magenta and cyan which are complementary colors of the blue, green and red are used. For example, acylacetanilide or benzoylmethane-based couplers are used to form a yellow image; pyrazolone, pyrazolobenzimidazole, cyanoacetophenone or indazolone-based couplers are mainly used to form a magenta image; and phenol-based couplers, such as phenols and naphthols, are used to form a cyan image.

Usually, color photographic light-sensitive materials can be divided roughly into two groups: (1) a coupler-in-developer system in which the couplers are incorporated in a developer, and (2) a coupler-in-emulsion system in which the couplers are incorporated in the respective light-sensitive layers of the light-sensitive material so that they can exhibit their functions independently. In the latter system, the coupler to form the corresponding dye image is added to a silver halide emulsion. It is required for the coupler added to the emulsion to be made non-diffusing or fast to diffusion in the emulsion binder matrix.

In the coupler-in-emulsion system, the processing of the color photographic light-sensitive material comprises fundamentally the following three steps:

(1) Color development,
(2) Bleaching, and
(3) Fixing.

The bleaching and fixing steps can be performed simultaneously; that is, a bleach-fixing step (so-called blix) can be employed. At this step, developed silver and silver halide not developed are removed. The practical development involves auxiliary steps to be applied for various purposes of, e.g., holding the photographic and physical quality of the image and improving the storage stability of the image, as well as the two fundamental steps, color development and desilvering, as described above. Examples of such auxiliary steps include a hardening bath which is used to prevent excessive softening of the light-sensitive film during the processing, a stop bath which is used to stop effectively the development, an image-stabilizing bath which is used to stabilize the image, and a film-removing bath which is used to remove the backing layer of the support.

In color photographic light-sensitive materials as described above, the compounds of the invention are generally added to the emulsions in combination with the color couplers of the coupler-in-emulsion system.

For this purpose, a method of adding the couplers to the emulsions or dispersing the couplers in the emulsions and a method of adding the couplers to the gelatin/silver halide emulsions or hydrophilic colloids can be employed. Typical examples of methods which can be employed include:

a method as described in, for example, U.S. Pat. Nos. 2,304,939 and 2,322,027, in which couplers are mixed with high boiling organic solvent-dibutyl phthalate, tricresyl phosphate, wax, higher fatty acids or their esters, and the like, and dispersed therein:

a method in which couplers are mixed with low boiling organic solvents or water-soluble organic solvents and dispersed therein;

a method as described in, for example, U.S. Pat. Nos. 2,801,170, 2,801,171 and 2,949,360 in which high boiling organic solvents are used in combination with the solvents as described in the foregoing method and dispersed therein; and a method as described in, for example, German Pat. No. 1,143,707 in which when couplers themselves have sufficiently low boiling points (e.g., 75° C. or lower), they are dispersed singly or in combination with other couplers, e.g., colored couplers or uncolored couplers.

Dispersion aids which can be used are those surfactants usually used, such as anionic surfactants (e.g., sodium alkylbenzenesulfonate, sodium dioctylsulfosuccinate, sodium dodecylsulfonate, sodium alkylnaphthalenesulfonate, and Fischer type couplers), amphoteric surfactants (e.g., N-tetradecyl-N,N-dipolyethylene α-betaine), and nonionic surfactants (e.g., sorbitan monolaurate).

Known couplers as described below can be used in combination with the compounds of the invention.

Suitable examples of magenta couplers are described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908, 3,891,445, West German Pat. No. 1,810,464, West German Patent Application (OLS) Nos. 2,408,665, 2,417,945, 2,418,959, 2,424,467, Japanese Patent Publication No. 6031/65, Japanese Patent Application (OPI) Nos. 20826/76, 58922/77, 129538/74, 74027/74, 159336/75, 42121/77, 74028/74, 60233/75, 26541/76, 55122/78, etc. (the term "OPI" as used herein refers to a "published unexamined Japanese patent application").

Suitable examples of yellow couplers are described in U.S. Pat. Nos. 2,875,057, 3,265,506, 3,408,194, 3,551,155, 3,582,322, 3,725,072, 3,891,445, West German Patent No. 1,547,868, West German Patent Application (OLS) Nos. 2,219,917, 2,261,361, 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77, 115219/77, etc.

Suitable examples of cyan couplers are described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411, 4,004,929, West German Patent Application (OLS) Nos. 2,414,830, 2,454,329, Japanese Patent Application (OPI) Nos. 59838/73, 26034/76, 5055/73, 146828/76, 69624/77, 90932/77, etc.

Colored couplers which can be used are those compounds as described in, for example, U.S. Pat. Nos. 3,476,560, 2,521,908, 3,034,892, Japanese Patent Publication Nos. 2016/69, 22335/63, 11304/67, 32461/69, Japanese Patent Application (OPI) Nos. 26034/76, 42121/77, West German Patent Application (OLS) No. 2,418,959, etc.

DIR couplers which can be used are those compounds as described in, for example, U.S. Pat. Nos. 3,227,554, 3,617,291, 3,701,783, 3,790,384, 3,632,345, West German Patent Application (OLS) Nos. 2,414,006, 2,454,301, 2,454,329, British Pat. No. 953,454, Japanese Patent Application (OPI) Nos. 69624/77, 122335/74, Japanese Patent Publication No. 16141/76, etc.

In addition to the DIR couplers, compounds releasing a development inhibitor as the development proceeds may be incorporated in the light-sensitive material. Examples of the compounds which can be used are described in, for example, U.S. Pat. Nos. 3,297,445, 3,379,529, West German Patent Application (OLS) No. 2,417,914, Japanese Patent Application (OPI) Nos. 15271/77 and 9116/78.

High boiling organic solvents which can be used are described in, for example, U.S. Pat. Nos. 2,322,027, 2,533,514, 2,835,579, Japanese Patent Publication No. 23233/71, U.S. Pat. No. 3,287,134, British Pat. No. 958,441, Japanese Patent Application (OPI) No. 1031/72, British Pat. No. 1,222,753, U.S. Pat. No. 3,936,303, Japanese Patent Application (OPI) Nos. 26037/76, 82078/75, U.S. Pat. Nos. 2,353,262, 2,852,383, 3,554,755, 3,676,137, 3,676,142, 3,700,454, 3,748,141, 3,837,863, West German Patent Application (OLS) No. 2,538,889, Japanese Patent Application (OPI) Nos. 27921/76, 27922/76, 26035/76, 26036/76, 62632/75, Japanese Patent Publication No. 29461/74, U.S. Pat. Nos. 3,936,303, 3,748,141, and Japanese Patent Application (OPI) No. 1521/78.

The compounds of the invention can be used in various types of instant photographs, including a system using the dye developers as described in, for example, U.S. Pat. Nos. 3,134,764, 3,173,929, 3,929,848 and 3,706,557, and a system releasing the diffusible dyes as described in, for example, U.S. Pat. Nos. 4,076,529, 4,135,929 and 4,013,635.

The compounds of the invention can be used also in a silver dye-bleaching method as described in, for example, *The Theory of the Photographic Process*, Chapter 12, *Principles and Chemistry of Color Photography* IV, Silver Dye Bleach Process, 4th Ed., T. H. Japes ed., Macmillan, New York (1977).

Moreover, the compounds of the invention can be used in black-and-white light-sensitive materials.

It is preferred for the compounds of the invention to be added to the silver halide emulsion layer or its adjacent layer. The amount of the compound being added is preferably from $1 \times 10^{-7}$ to $1 \times 10^{-1}$ mol per mol of silver.

It is preferred that the compound of the invention be emulsified and dispersed, and added to a coating solution in the same manner as in the case of color couplers.

It is advantageous to use gelatin as a binder or protective colloid for the photographic emulsion. In addition, other hydrophilic colloids can be used.

Examples are gelatin derivatives, graft polymers of gelatin and other polymers, proteins, e.g., albumin and casein, cellulose derivatives, e.g., hydroxyethyl cellulose, carboxymethyl cellulose, and cellulose sulfate, saccharide derivatives, e.g., sodium alginate and starch derivatives, and a number of synthetic hydrophilic polymeric substances, e.g., homo- and copolymers such as polyvinyl alcohol, polyvinyl alcohol partial acetal, poly(N-vinyl) pyrrolidone, polyacrylic acid, polymethacrylic acid, polyacrylamide, polyvinyl imidazole and polyvinyl pyrazole.

As the gelatin, as well as lime-treated gelatin, acid-treated gelatin and enzyme-treated gelatin as described in *Bull. Soc. Sci. Phot. Japan*, No. 16, page 30 (1966) can be used. In addition, hydrolyzates and enzyme decomposition products of gelatin can be used. Gelatin derivatives which can be used are prepared by reacting gelatin with various compounds such as acid halides, acid anhydrides, isocyanates, bromoacetic acid, alkanesultones, vinylsulfonamides, maleinimides, polyalkylene oxides, and epoxy compounds.

Any of silver bromide, silver iodobromide, silver iodochlorobromide, silver chlorobromide and silver chloride can be used as silver halide for the photographic emulsions as used herein.

The mean grain size of silver halide grains in the photographic emulsion is preferably 5μ or less and particularly preferably 3μ or less. The mean grain size is determined on basis of the corresponding volumetric average in any of grains which are spherical or nearly spherical, in a regular form, e.g., cubic and octahedral, or in a plate-like form.

The grain size distribution may be narrow or broad.

Silver halide grains in the photographic emulsion may have a regular crystal form, e.g., a cube and an octahedron, an irregular crystal form, e.g., a sphere and a plate, or a composite crystal form thereof. A mixture of grains having different crystal forms can also be used.

These silver halide grains may have a structure comprising an inner portion and a surface layer which are different in phase, or may be composed of a uniform phase. Moreover, they may be those grains in which a latent image is formed mainly on the surface thereof, or may be those grains in which a latent image is formed mainly in the interior thereof.

Photographic emulsions as used herein can be prepared in any suitable manner, such as by the methods described in, for example, P. Glafkides, *Chimie et Physique Photographique*, Paul Montel (1967), G. F. Duffin, *Photographic Emulsion Chemistry*, The Focal Press Co. (1966), and V. L. Zelikman et al., *Making and Coating Photographic Emulsion*, The Focal Press Co. (1964). That is, any of the acidic process, the neutral method, and the ammonia method, etc., can be employed. Moreover, soluble silver salts and soluble halides can be reacted by any of the single jet method, the double jet method, and a combination thereof.

In addition, a so-called reverse mixing method in which silver halide grains are formed in the presence of excess of silver ions can be employed. As one embodiment of the simultaneous mixing method, a so-called controlled double jet method in which pAg in the liquid phase where silver halide is formed is maintained at a constant level can be employed.

In accordance with this method, a silver halide emulsion in which the crystal form is regular and the grain size is nearly uniform can be obtained.

Two or more silver halide emulsions which are prepared independently may be used in admixture with each other.

In the course of the formation of silver halide grains or physical ripening thereof, cadmium salts, zinc salts, lead salts, thallium salts, iridium salts or its complex salts, rhodium salts or its complex salts, iron salts or its complex salts, and the like may coexist.

In order to remove soluble salts from the emulsion after the precipitate formation or physical ripening, a nudel rinsing method may be employed in which gelatin is caused to gel. In addition, a flocculation method utilizing inorganic salts, anionic surfactants, anionic polymers (e.g., polystyrenesulfonic acid), or gelatin derivatives (e.g., acylated gelatin and carbamoylated gelatin) may be used.

Silver halide emulsions are usually subjected to chemical sensitization. This chemical sensitization can be applied by the methods described in, for example, H. Frieser ed., *Die Grundlagen der Photographischen Prozesse mit Silberhalogeniden*, Akademische Verlagsgesellschaft, pp. 675–734 (1968). That is, a sulfur sensitization method using compounds capable of reacting with active gelatin or silver (e.g., thiosulfates, thioureas, mercapto compounds, and rhodanines), a reduction sensitization method using reducing substances (e.g., stannous salts, amines, hydrazine derivatives, formamidinesulfinic acid, and silane compounds), a noble metal sensitization method using noble metal compounds (e.g., gold complex salts, and complex salts of the metals (e.g., Pt, Ir and Pd) of Group VIII of the Periodic Table), and so forth can be used singly or in combination with each other.

The sulfur sensitization method is described in detail in U.S. Pat. Nos. 1,574,944, 2,410,689, 2,278,947, 2,728,668, 3,656,955, etc.; the reduction sensitization method is described in detail in U.S. Pat. Nos. 2,983,609, 2,419,974, 4,054,458, etc.; and the noble metal sensitization method is described in detail in U.S. Pat. Nos. 2,399,083, 2,448,060, British Pat. No. 618,061, etc.

For the purpose of preventing fog or stabilizing photographic performance during the production, the storage or the photographic processing of the light-sensitive material, various compounds can be incorporated in the photographic emulsions as used herein. That is, a number of compounds known as antifoggants or stabilizers can be added, including azoles such as benzothiazolium salts, nitroindazoles, triazoles, benzotriazoles, and benzimidazoles (particularly nitro- or halogen-substituted products); heterocyclic mercapto compounds such as mercaptothiazoles, mercaptobenzothiazoles, mercaptobenzimidazoles, mercaptothiadiazoles, mercaptotetrazoles (particularly 1-phenyl-5-mercaptotetrazole) and mercaptopyrimidine; the foregoing heterocyclic mercapto compounds further containing a water-soluble group, e.g., a carboxyl group and a sulfo group; thioketo compounds such as oxazolinthione; azaindenes such as tetraazaindenes (particularly 4-hydroxy-substituted(1,3,3a,7)tetraazaindenes); benzenethiosulfonic acid; and benzenesulfinic acid.

Various surfactants may be incorporated in the photographic emulsion layer or other hydrophilic colloid layer of the light-sensitive material of the invention as auxiliary coating agents or for various purposes, such as to prevent charging, to improve sliding properties, and emulsification and dispersion, to prevent adhesion or to improve photographic characteristics (e.g., acceleration of development, high contrast and sensitization).

For example, nonionic surfactants such as saponin (steroids), alkylene oxide derivatives (e.g., polyethylene glycol, a polyethylene glycol/polypropylene glycol condensate, polyethylene glycol alkyl ethers or polyethylene glycol alkylaryl ethers, polyethylene glycol esters, polyethylene glycol sorbitan esters, polyalkylene glycol alkylamines or amides, and silicone/polyethylene oxide adducts), glycidol derivatives (e.g., alkenylsuccinic acid polyglyceride and alkylphenol polyglyceride), fatty acid esters of polyhydric alcohols, and alkyl esters of saccharides; anionic surfactants containing acidic groups, e.g., a carboxyl group, a sulfo group, a phospho group, a sulfate group, and a phosphate group, such as alkylcarboxylates, alkylsulfonates, alkylbenzenesulfonates, alkylnaphthalenesulfonates, alkylsulfates, alkylphosphates, N-acyl-N-alkyltaurines, sulfosuccinates, sulfoalkylpolyoxyethylene alkylphenyl ethers, and polyoxyethylene alkylphosphates; amphoteric surfactants such as amino acids, aminoalkylsulfonic acids, aminoalkylsulfates, or phosphates, alkylbetaines, and amine oxides; and cationic surfactants such as alkylamine salts, aliphatic or aromatic quaternary ammonium salts, heterocyclic quaternary ammonium salts, e.g., pyridinium and imidazolium, and aliphatic or heterocyclic ring-containing phosphonium or sulfonium salts can be used.

For the purpose of increasing sensitivity or contrast, or accelerating development, polyalkylene oxides or their ether, ester, amine or like derivatives, thioether compounds, thiomorpholines, quaternary ammonium salt compounds, urethane derivatives, urea derivatives, imidazole derivatives, 3-pyrazolidones, etc., may be added to the photographic emulsion layer of the light-sensitive material of the invention. Typical examples of such compounds are described in, for example, U.S. Pat. Nos. 2,400,532, 2,423,549, 2,716,062, 3,617,280, 3,772,021, 3,808,003 and British Pat. No. 1,488,991.

In the photographic processing of the light-sensitive material of the invention, the known methods and known processing solutions as described in, for example, Research Disclosure, No. 176, pp. 28–30 (RD-17643) can be used. This photographic processing may be either a black-and-white photographic processing to form a silver image, or a color photographic processing to form a dye image depending on the purpose.

The processing temperature is usually chosen within the range of from 18° to 50° C., although it can be performed at lower temperatures than 18° C. or higher temperatures than 50° C.

The developer for use in the black-and-white photographic processing can contain known developing agents. Developing agents which can be used include dihydroxybenzenes (e.g., hydroquinone), 3-pyrazolidones (e.g., 1-phenyl-3-pyrazolidone), and aminophenols (e.g., N-methyl-p-aminophenol). These compounds can be used singly or in combination with each other. In general, the developer contains other known additives such as a preservative, an alkali agent, a pH buffer, and an antifoggant. In addition, if desired, it may contain an auxiliary dissolving agent, a color tone controller, a development promoter, a surfactant, a defoaming agent, a water-softening agent, a hardener, a tackifier, etc.

The so-called lith type of development can be applied to the photographic emulsion of the invention. This lith type of development means a method in which for photographic reproduction of line images or photographic reproduction of half tone images utilizing dots, dihydroxybenzenes are usually employed as the developing agent and the development is performed infectiously at a low sulfite ion concentration. The details of the lith type of development are described in F. A. Mason, *Photographic Processing Chemistry*, pp. 163–165 (1966).

As a specific developing procedure, a method may be employed in which the developing agent is incorporated in the light-sensitive material, for example, in the emulsion layer thereof and the light-sensitive material is developed by treating with an alkali aqueous solution. Hydrophobic compounds of the developing agents can be incorporated in the emulsion layer by various techniques, such as by the methods described in *Research Disclosure*, No. 169 (RD-16928), U.S. Pat. No. 2,739,890, British Pat. No. 813,253, and West German Pat. No. 1,547,763. Such a photographic processing may be conducted in combination with a silver salt-stabilizing treatment using thiocyanates.

As fixing solutions, those having compositions commonly used can be employed. As fixing agents, as well as thiosulfates and thiocyanates, organic sulfur compounds known to be effective as fixing agents can be employed. The fixing solution may contain water-soluble aluminum salts as a hardener.

Dye images can be formed by the usual methods. For example, a negative positive process (described in, for example, *Journal of the Society of Motion Picture and Television Engineers*, Vol. 61, pp. 667–701 (1953)); a color reversion process in which a negative silver image is formed by developing with a developer containing a black-and-white developing agent, is subjected to at least one uniform exposure or other suitable fog treatments, and subsequently, is color developed to form a dye positive image; and a silver dye bleaching process in which a photographic emulsion layer containing dye is exposed and then developed to form a silver image, and the dye is bleached with the silver image thus formed as a bleaching catalyst; and so forth can be employed.

A color developer generally comprises an alkaline aqueous solution containing a color developing agent. As color developing agents, the known primary aromatic amine developers, e.g., phenylenediamines such as 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfonamidoethylaniline and 4-amino-3-methyl-N-ethyl-N-β-methoxyethylaniline, can be used.

In addition, the compounds as described in, for example, L. F. A. Mason, *Photographic Processing Chemistry*, pp. 226–229, Focal Press Co. (1966), and U.S. Pat. Nos. 2,193,015 and 2,592,364, and Japanese Patent Application (OPI) No. 64933/73 can be used.

The color developer can further contain a pH buffer, a development inhibitor, an antifoggant, and so forth. If desired, a water-softening agent, a preservative, an organic solvent, a development promoter, a dye-forming coupler, a competitive coupler, a foggant, an auxiliary developing agent, a tackifier, a carboxylic acid-based chelating agent, an antioxidant, and so forth may be added.

Suitable examples of such additives are described in, for example, *Research Disclosure* (RD-17643), U.S. Pat. No. 4,083,723, and West German Patent Application (OLS) No. 2,622,950.

After color development, the photographic emulsion layer is usually bleached. This bleaching may be performed simultaneously with a fixing treatment, or they may be performed separately. Bleaching agents which can be used include compounds of multivalent metals, e.g., iron (III), cobalt (III), chromium (VI) and copper (II), peracids, quinones and nitroso compounds.

Examples are ferricyanides, dichromates, organic complex salts of iron (III) or cobalt (III) with aminopolycarboxylic acids (such as ethylenediaminetetraacetic acid, nitrilotriacetic acid and 1,3-diamino-2-propanoltetraacetic acid) or organic acids (such as citric acid, tartaric acid and malic acid), persulfates, permanganates and nitrophenol. Of these compounds, potassium ferricyanide, sodium ethylenediaminetetraacetate iron (III) and ammonium ethylenediaminetetraacetate iron (III) are particularly useful. Iron (III) complex salts of ethylenediaminetetraacetic acid are useful in both the independent bleaching solution and the monobath bleach-fixing solution.

To the bleaching or bleach-fixing solution can be added the bleach accelerators as described in U.S. Pat. Nos. 3,042,520, 3,241,966, Japanese Patent Publication Nos. 8506/70, 8836/70, etc., the thiol compounds as described in Japanese Patent Application (OPI) No. 65732/78, etc., and other various additives.

The light-sensitive material of the invention may be processed with a developer which is replenished or controlled by the methods as described in Japanese Patent Application (OPI) Nos. 84636/76, 119934/77, 46732/78, 9626/79, 19741/79, 37731/79, 1048/81, 1049/81 and 27142/81.

The bleach-fixing solution to be used for the light-sensitive material of the invention may be regenerated by the methods as described in Japanese Patent Application (OPI) Nos. 781/71, 49437/73, 18191/73, 145231/75, 18541/76, 19535/76 and 144620/76, and Japanese Patent Publication No. 23178/76.

The light-sensitive material of the invention may contain a dispersion of water-insoluble or sparingly soluble synthetic polymer for the purpose of improving dimensional stability in the photographic emulsion layer and other hydrophilic colloid layers thereof. Examples of such synthetic polymers are homo- and copolymers of alkyl acrylate or methacrylate, alkoxyalkyl acrylate or methacrylate, glycidyl acrylate or methacrylate, acrylamide or methacrylamide, vinyl ester (e.g., vinyl acetate), acrylonitrile, olefins, styrene and so forth, and copolymers of the foregoing monomers with acrylic acid, methacrylic acid, $\alpha,\beta$-unsaturated dicarboxylic acid, hydroxyalkyl acrylate or methacrylate, sulfoalkyl acrylate or methacrylate, and styrenesulfonic acid. For example, the polymers as described in U.S. Pat. Nos. 2,376,005, 2,739,137, 2,853,457, 3,062,674, 3,411,911, 3,488,708, 3,525,620, 3,607,290, 3,635,715, 3,645,740, British Pat. Nos. 1,186,699 and 1,307,373.

The photographic emulsions as used herein may be subjected to spectral sensitization using methine dyes and the like.

Useful sensitizing dyes are described in, for example, German Pat. No. 929,080, U.S. Pat. Nos. 2,493,748, 2,503,776, 2,519,001, 2,912,329, 3,656,959, 3,672,897, 4,025,349, British Pat. No. 1,242,588, and Japanese Patent Publication No. 14030/69.

These sensitizing dyes may be used singly or in combination with each other. Combinations of the sensitizing dyes are often employed particularly for supersensitization. Typical examples of such supersensitization are described in U.S. Pat. Nos. 2,688,545, 2,977,229, 3,397,060, 3,522,052, 3,527,641, 3,617,293, 3,628,964, 3,666,480, 3,672,898, 3,679,428, 3,814,609, 4,026,707, British Pat. No. 1,344,281, Japanese Patent Publication Nos. 4936/68, 12375/78, Japanese Patent Application (OPI) Nos. 110618/77 and 109925/77.

In the preparation of the light-sensitive material of the invention, the photographic emulsion layers and other layers are coated on flexible supports, e.g., a plastic film, paper and cloth, or rigid supports made of, e.g., glass, porcelain and metal, which are commonly used in the preparation of the usual photographic light-sensitive materials. Useful examples of such flexible supports are films made of semi-synthetic or synthetic polymers, such as cellulose nitrate, cellulose acetate, cellulose acetate butyrate, polystyrene, polyvinyl chloride, polyethylene terephthalate, and polycarbonate, and paper provided with a baryta layer or coated or laminated with $\alpha$-olefin polymers (e.g., polyethylene, polypropylene and an ethylene/butene copolymer). These supports may be colored with dyes or pigments. For the purpose of shielding light, they may be colored black. The surface of the support is usually coated with a subbing layer in order to improve the adhesion to the photographic layers, and the like. Before or after the coating of the subbing layer, the surface of the support may be subjected to corona discharge, irradiation with ultraviolet rays, flame treatment, and so forth.

In the preparation of the light-sensitive material of the invention, the photographic emulsion layers and other hydrophilic colloid layers can be coated on the support or other layers by various known techniques such as dip coating, roller coating, curtain coating and extrusion coating. It is advantageous to use the methods as described in U.S. Pat. Nos. 2,681,294, 2,761,791 and 3,526,528.

The present invention is applicable to multilayer multicolor photographic materials having at least two different spectral sensitivites. A multilayer natural color photographic material usually comprises a support and at least one of each of red-sensitive, green-sensitive and blue-sensitive emulsion layers provided on the support. The order in which the layers are provided can be changed or determined optionally. It is usual to incorporate the cyan-forming coupler in the red-sensitive emulsion layer, the magenta-forming coupler in the green-sensitive emulsion layer, and the yellow-forming coupler in the blue-sensitive emulsion layer. In some cases, however, different combinations may be employed.

The light-sensitive material of the invention is exposed to light in the usual manner to obtain a photographic image. For this exposure, any of a number of known light sources, e.g., natural light (sunlight), a tungsten lamp, a fluorescent lamp, a mercury lamp, a xenon arc lamp, a carbon arc lamp, a xenon flash lamp, and a cathode ray tube flying spot can be used. The exposure time may be from 1/1,000 to 1 second, which is usually employed for cameras. Moreover, an exposure time of shorter than 1/1,000 second, for example, an exposure time of from $1/10^4$ to $1/10^6$ second using a xenon flash lamp or a cathode ray tube can be employed. Additionally, the light-sensitive material may be exposed to light for more than 1 second. If desired, a color filter may be used to control the spectral composition of light for use in exposure. A laser light can be used for exposure. Moreover, the light-sensitive material of the invention may be exposed to light generated from a fluorescent body which is excited by electron rays, X-rays, $\alpha$-rays, or $\beta$-rays.

In the light-sensitive material of the invention, the photographic emulsion layers and other hydrophilic colloid layers may contain whiteners, such as stilbene-, triazine-, oxazole-, or cumarin-based whiteners. These compounds may be water-soluble, or water-insoluble whiteners may be used in the form of a dispersion.

The light-sensitive material of the invention may contain inorganic or organic hardeners in the photographic emulsion layers and other hydrophilic colloid layers thereof. Examples of hardeners which can be used are chromium salts (e.g., chromium alum and chromium acetate), aldehydes (e.g., formaldehyde, glyoxal, and glutaraldehyde), N-methylol compounds (e.g., dimethylolurea and methyloldimethyl hydantoin), dioxane derivatives (e.g., 2,3-dihydroxydioxane), active vinyl compounds (e.g., 1,3,5-triacryloyl-hexahydro-s-triazine and 1,3-vinylsulfonyl-2-propanol), active halogen compounds (e.g., 2,4-dichloro-6-hydroxy-s-triazine), and mucohalogenic acids (e.g., mucochloric acid and mucophenoxychloric acid). These compounds can be used singly or in combination with each other.

In the light-sensitive material of the invention, when dyes, ultraviolet absorbers, etc., are contained in the hydrophilic colloid layers, they may be, for example, mordanted with cationic polymers. Examples of such polymers are described in British Pat. No. 685,475, U.S. Pat. Nos. 2,675,316, 2,839,401, 2,882,156, 3,048,487, 3,184,309, 3,445,231, West German Patent Application (OLS) No. 1,914,362, Japanese Patent Application (OPI) Nos. 47624/75 and 71332/75.

The light-sensitive material of the invention may contain hydroquinone derivatives, aminophenol derivatives, gallic acid derivatives, ascorbic acid derivatives and so forth as color antifoggants.

The light-sensitive material of the invention may contain ultraviolet absorbers in the hydrophilic colloid layers thereof. Ultraviolet absorbers which can be used are benzotriazole compounds substituted by an aryl group, 4-thiazolidone compounds, benzophenone compounds, cinnamate compounds, butadiene compounds and benzoxazole compounds and polymers capable of absorbing ultraviolet rays. These ultraviolet absorbers may be fixed in the foregoing hydrophilic colloid layers.

In the practice of the present invention, the known anti-fading agents as described hereinafter may be used in combination. Color image-stabilizers can be used singly or as a mixture comprising two or more thereof. The known anti-fading agents include hydroquinone derivatives, gallic acid derivatives, p-alkoxyphenols, p-oxyphenol derivatives and bisphenols.

The light-sensitive material of the invention may contain water-soluble dyes as filter dyes or for various purposes, e.g., for prevention of irradiation, in the hydrophilic colloid layer thereof. Examples of such dyes include oxonol dyes, hemioxonol dyes, styryl dyes, merocyanine dyes, cyanine dyes, and azo dyes. Of these compounds, oxonol dyes, hemioxonol dyes and merocyanine dyes are useful.

The present invention is described in detail with reference to the following examples, although it is not intended to be limited thereto.

EXAMPLE 1

A cellulose triacetate film support provided with a subbing layer was coated with an emulsion prepared by adding an auxiliary developing agent or its precursor to a high boiling organic solvent as shown in Table 1. In this way, Samples 1 to 10 were prepared. The amount of each compound being added is shown in parenthesis ($g/m^2$ or $mol/m^2$).

(1) Emulsion Layer

Negative type silver iodobromide emulsion (mean particle size of AgX: $1.5\mu$) (silver coverage: $1.6 \times 10^{-2}$ $mol/m^2$);

Magenta coupler[1] ($1.33 \times 10^{-3}$ $mol/m^2$);

Auxiliary developing agent or its precursor ($1.33 \times 10^{-3}$ $mol/m^2$);

Gelatin ($2.50$ $g/m^2$).

(2) Protective Layer

Gelatin ($1.30$ $g/m^2$);

These films were subjected to imagewise exposure for sensitometry and then to color development processings as described below.

| Color Developing Processings | Time | Temperature (°C.) |
|---|---|---|
| 1. Color Development | 3 min. 15 sec. | 38 |
| 2. Bleaching | 6 min. 30 sec. | " |
| 3. Water Washing | 2 min. | " |
| 4. Fixing | 4 min. | " |
| 5. Water Washing | 4 min. | " |
| 6. Stabilization | 1 min. | " |

The composition of each processing solution used at the color developing steps is as follows:

| Color Developer | |
|---|---|
| Water | 800 ml |
| 4-(N—Ethyl-N—hydroxyethyl)amino-2-methylaniline sulfate | 5 g |
| Sodium sulfite | 5 g |
| Hydroxylamine sulfate | 2 g |
| Potassium carbonate | 30 g |
| Potassium hydrogencarbonate | 1.2 g |
| Potassium bromide | 1.2 g |
| Sodium chloride | 0.2 g |
| Trisodium nitrilotriacetate | 1.2 g |
| Water to make | 1,000 ml |
| | (pH, 10.1) |
| Bleaching Solution | |
| Water | 800 ml |
| Iron (III) ammonium ethylenediaminetetraacetate | 100 g |
| Disodium ethylenediaminetetraacetate | 10 g |
| Potassium bromide | 150 g |
| Acetic acid | 10 g |
| Water to make | 1,000 ml |
| | (pH, 6.0) |
| Fixing Solution | |
| Water | 800 ml |
| Ammonium thiosulfate | 150 g |
| Sodium sulfite | 10 g |
| Sodium hydrogensulfite | 2.5 g |
| Water to make | 1,000 ml |
| | (pH, 6.0) |
| Stabilizing Solution | |
| Water | 800 ml |
| Formalin (37% aq. soln.) | 5 ml |
| Fuji Driwel | 3 ml |
| Water to make | 1,000 ml |

The photographic properties are shown in Table 1.

TABLE 1

| Sample No. | Test Compound | Fog | Gamma | Relative* Sensitivity | Maximum Color Density |
|---|---|---|---|---|---|
| 1 | — | 0.13 | 0.64 | 100 | 1.40 |
| 2 | Comparative Compound (D-1) | 0.20 | 0.85 | 79 | 1.52 |
| 3 | Comparative Compound (D-2) | 0.25 | 0.83 | 82 | 1.59 |
| 4 | Comparative Compound (D-3) | 0.18 | 0.79 | 92 | 1.55 |
| 5 | Comparative Compound (D-4) | 0.19 | 0.80 | 94 | 1.60 |
| 6 | Compound (21) of the Invention | 0.14 | 0.76 | 126 | 1.60 |
| 7 | Compound (7) of the Invention | 0.13 | 0.72 | 121 | 1.57 |
| 8 | Compound (9) of the Invention | 0.14 | 0.77 | 138 | 1.58 |
| 9 | Compound (4) of the Invention | 0.14 | 0.76 | 123 | 1.57 |

TABLE 1-continued

| Sample No. | Test Compound | Fog | Gamma | Relative* Sensitivity | Maximum Color Density |
|---|---|---|---|---|---|
| 10 | Compound (22) of the Invention | 0.13 | 0.70 | 117 | 1.55 |

*Relative sensitivity: This is a reciprocal of an exposure amount necessary to provide a color density of fog + 0.2 and is given as a relative value with the sensitivity of Sample 1 as being 100.

It can be seen from Table 1 that for the samples containing the auxiliary developing agent precursors of the invention, almost no increase in fog is involved, and all the gamma, sensitivity and color density are increased.

The magenta coupler and auxiliary developing agents as used herein are as follows:

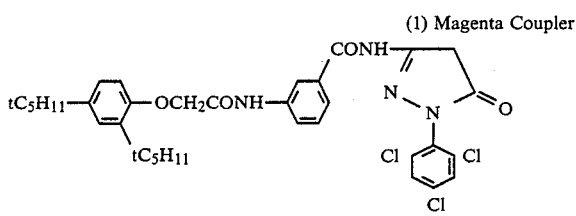
(1) Magenta Coupler

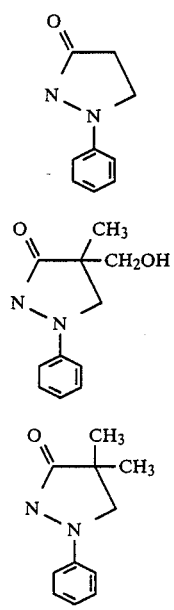

Comparative Compound (D-1)

Comparative Compound (D-2)

Comparative Compound (D-3)

Comparative Compound (D-4)

EXAMPLE 2

In this example, the effectiveness of the antifoggant precursors of the invention was evaluated. A cellulose triacetate film support provided with a subbing layer was coated with an emulsion prepared by adding an antifoggant or its precursor as shown in Table 2 to a coupler solvent in combination with a coupler. In this way, Samples 11 to 17 were prepared. The amount of each substance being coated is shown in parenthesis (g/m² or mol/m²).

(1) Emulsion Layer

Negative type silver iodobromide emulsion (mean particle size of AgX: $1.5\mu$) (silver coverage: $1.6 \times 10^{-2}$ mol/m$^2$);

Magenta coupler (the same as used in Example 1) ($1.33 \times 10^{-3}$ mol/m$^2$);

Antifoggant or its precursor (as shown in Table 2) Gelatin (2.50 g/m$^2$).

(2) Protective Layer
Gelatin (1.30 g/m$^2$)

These films were subjected to imagewise exposure for sensitometry and then were subjected to the same developing processings as in Example 1.

The photographic properties are shown in Table 2.

TABLE 2

| Sample No. | Anti-foggant | Coating Amount (ml/m²) | Fog | Gamma | Relative** Sensitivity | Maximum Color Density |
|---|---|---|---|---|---|---|
| 11 | — | — | 0.13 | 0.65 | 100 | 1.41 |
| 12 | A-1 | $8.0 \times 10^{-4}$ | 0.06 | 0.27 | 55 | 0.75 |
| 13* | (12) | $8.0 \times 10^{-4}$ | 0.08 | 0.66 | 101 | 1.35 |
| 14 | A-2 | $5.3 \times 10^{-6}$ | 0.04 | 0.16 | 43 | 0.74 |
| 15* | (8) | $5.3 \times 10^{-6}$ | 0.07 | 0.62 | 100 | 1.31 |
| 16 | A-3 | $1.1 \times 10^{-4}$ | 0.04 | 0.23 | 49 | 0.82 |
| 17* | (20) | $1.1 \times 10^{-4}$ | 0.08 | 0.65 | 99 | 1.30 |

*Samples 13, 15, 17: Examples of the Invention
**Relative sensitivity: This is a reciprocal of an exposure amount necessary to provide a color density of fog + 0.2 and is given as a relative value with the sensitivity of Sample 11 as being 100.

It can be seen from Table 2 that if the antifoggants are added as such, the formation of fog can be prevented, but the sensitivity and color density drop, whereas the antifoggant precursors of the invention make it possible to reduce fog with almost no deterioration in sensitivity and color density.

The antifoggants as used herein are as follows:

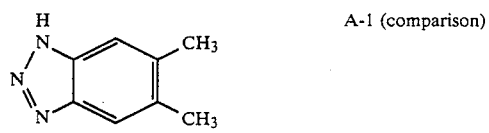
A-1 (comparison)

A-2 (comparison)

A-3 (comparison)

EXAMPLE 3

In this example, the effectiveness of the auxiliary developing agent precursors of the invention was evaluated. A paper support which had been laminated with polyethylene on both sides was coated with an auxiliary developing agent or its precursor as shown in Table 3 in the same manner as in Example 1. In this way, Samples 18 to 24 were prepared.

(1) Emulsion Layer

Negative type silver chlorobromide emulsion (mean particle size of AgX: $0.7\mu$) (silver coverage: $5.12 \times 10^{-3}$ mol/m$^2$);

Yellow coupler$^{(2)}$ ($8.53 \times 10^{-4}$ mol/m$^2$);

Auxiliary developing agent or its precursor ($5.12 \times 10^{-4}$ mol/m$^2$);

Gelatin (1.35 g/m$^2$).

(2) Protective Layer

Gelatin (1.30 g/m$^2$);

These films were subjected to imagewise exposure for sensitometry and then to the following color development processings.

| Color Development Processings | Time | Temperature (°C.) |
|---|---|---|
| 1. Color Development | 2 min. | 33 |
| 2. Bleach-Fixing | 1 min. 30 sec. | 33 |
| 3. Water Washing | 2 min. 30 sec. | 25–30 |

The composition of each processing solution is shown below:

| Color Developer | |
|---|---|
| Benzyl alcohol | 15 ml |
| Diethylene glycol | 8 ml |
| Ethylenediaminetetraacetic acid | 5 g |
| Sodium sulfite | 2 g |
| Anhydrous potassium carbonate | 30 g |
| Hydroxylamine sulfate | 3 g |
| Potassium bromide | 0.6 g |
| 4-Amino-N—ethyl-N—(β-methanesulfonamidoethyl)-m-toluidine sesquisulfate (monohydrate) | 5 g |
| Water to make | 1,000 ml |
| | (pH, 10.20) |
| Bleach-Fixer | |
| Ethylenediaminetetraacetic acid | 2 g |
| Iron (III) ethylenediaminetetraacetate | 40 g |
| Sodium sulfite | 5 g |
| Ammonium thiosulfate | 70 g |
| Water to make | 1,000 ml |

The photographic properties are shown in Table 3.

TABLE 3

| Sample No. | Test Compound | Fog | Gamma | Relative*** Sensitivity |
|---|---|---|---|---|
| 18 | — | 0.05 | 2.15 | 100 |
| 19* | D-3 | 0.12 | 2.23 | 113 |
| 20* | D-2 | 0.11 | 2.25 | 106 |
| 21* | D-5 | 0.06 | 2.45 | 82 |
| 22** | (16) | 0.05 | 2.14 | 129 |
| 23** | (7) | 0.05 | 2.17 | 121 |
| 24** | (13) | 0.05 | 2.20 | 118 |

*Sample Nos. 19 to 21: Comparative examples
**Sample Nos. 22 to 24: Examples of the invention
***Relative sensitivity: This is a reciprocal of an exposure amount necessary to provide a color density of fog + 0.2 and is given as a relative value with the sensitivity of Sample 18 as being 100.

It can be seen from Table 3 that when the auxiliary developing agents are used, the formation of fog is involved through sensitization is attained, or desensitization is involved although fog is not increased, whereas the precursors of the invention make it possible to achieve sensitization without increasing fog.

The yellow couplers and auxiliary developing agents as used herein are as follows:

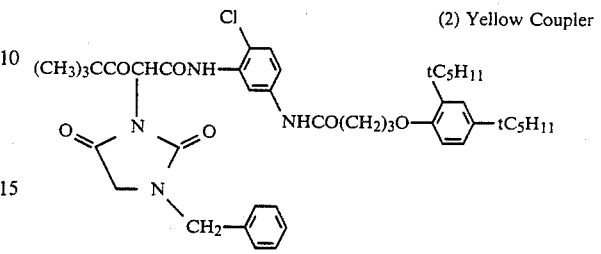

(2) Yellow Coupler

Same as used in Example 1

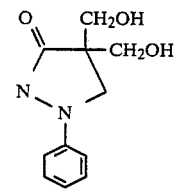

D-2, D-3:
D-5

EXAMPLE 4

Light-sensitive sheets and image-receiving sheet as described below were prepared.

Light-Sensitive Sheet

This light-sensitive sheet was prepared by coating an emulsion layer and a protective layer as described below on a polyethylene-laminated paper support. The compound of the invention (auxiliary developing agent precursor) and a comparative compound (auxiliary developing agent) were each dissolved in methyl alcohol and added to the emulsion layer.

(1) Emulsion Layer

Silver iodobromide emulsion containing 4% of silver iodide (silver: $9.2 \times 10^{-3}$ mol/m$^2$);

Compound of the invention and comparative compound ($1.0 \times 10^{-6}$ mol/m$^2$);

Gelatin (1.50 g/m$^2$).

(2) Protective Layer

Gelatin (1.0 g/m$^2$).

Image-Receiving Sheet

A polyethylene-laminated paper bearing a 6 μm thick cellulose triacetate layer was soaked in an alkaline hydrolytic solution containing silver precipitating nuclei for 1 minute to prepare a common diffusion transfer image-receiving sheet.

The alkaline hydrolytic solution as used above was prepared as follows:

Nickel nitrate (0.1 g) was dissolved in 2 ml of water and added to 100 ml of glycerine. A solution of 1 g of sodium sulfide dissolved in 2 ml of water was added to the mixture as prepared above while stirring vigorously to prepare a silver precipitating nucleus dispersion of nickel sulfide. Then, 20 ml of the dispersion as prepared above was added to 1,000 ml of a water/methyl alcohol (1:1) solution containing 80 g of sodium hydroxide to prepare the desired silver precipitating nucleus-containing alkaline hydrolytic solution.

The Light-Sensitive Sheets 1 to 7 as prepared above were subjected to imagewise exposure before and after holding under forced deterioration conditions (60° C., 3 days). A processing solution as described below was extended between the light-sensitive sheet and the image-receiving sheet in a thickness of 0.1 mm to conduct diffusion transfer development.

| Processing Solution | |
|---|---|
| Potassium hydroxide (40% aq. soln.) | 323 ml |
| Titanium dioxide | 3 g |
| Hydroxyethyl cellulose | 79 g |
| Zinc oxide | 9.75 g |
| N,N—Bismethoxyethylhydroxylamine | 75 g |
| Triethanolamine (45% aq. soln.) | 17.14 g |
| Tetrahydropyrimidinethione | 0.4 g |
| 2,4-Dimercaptopyrimidine | 0.35 g |
| Uracil | 90 g |
| Water | 1,193 ml |

The optical density of the transfer silver image thus obtained was measured, and a reciprocal of an exposure amount to obtain an optical density of 0.7 was given as a sensitivity value. This sensitivity is a relative sensitivity with respect to that of the control sample (Light-Sensitive Sheet No. 1, containing no additive and not placed under the forced deterioration conditions) as being 100. The results are shown in Table 4.

TABLE 4

| Light-Sensitive Sheet | Test Compound | Before Forced Deterioration | | After Forced Deterioration | |
|---|---|---|---|---|---|
| | | Sensitivity | Maximum Optical Density | Sensitivity | Maximum Optical Density |
| 1 | — | 100 | 1.60 | 90 | 1.45 |
| 2 | Comparative Compound (D-3) | 145 | 1.60 | 120 | 0.80 |
| 3 | Comparative Compound (D-1) | 130 | 1.54 | 100 | 0.62 |
| 4 | Comparative Compound (D-6) | 155 | 1.55 | 110 | 0.70 |
| 5* | Compound (16) | 125 | 1.62 | 120 | 1.48 |
| 6* | Compound (15) | 135 | 1.58 | 130 | 1.45 |
| 7* | Compound (11) | 120 | 1.60 | 120 | 1.46 |

*5, 6 and 7: Examples of the invention

Table 4 shows that Sheets 2 to 7 are all of higher sensitivity than the control sample, Sheet 1. In the comparative samples, Sheets 2 to 4, however, the maximum optical density under the forced deterioration conditions dropped seriously. On the other hand, the samples in which the precursors of the invention were added maintained their high sensitivity and there was only a slight reduction in color density.

With regard to the comparative compounds as used herein, D-1 and D-3 were the same as used in Example 1, and D-6 is as follows:

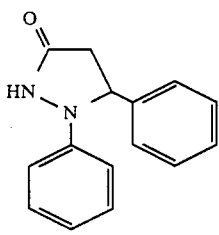

D-6

EXAMPLE 5

A multilayer color light-sensitive material was prepared by providing the layers as described hereinafter on a cellulose triacetate film support.

First Layer: Antihalation Layer (AHL)
A gelatin layer containing black colloidal silver.
Second Layer: Intermediate Layer (ML)
A gelatin layer containing a dispersion of 2,5-ditert-octylhydroquinone.
Third Layer: First Red-Sensitive Emulsion Layer (RL$_1$)

| | |
|---|---|
| Silver iodobromide emulsion (silver iodide: 5 mol %) | 1.79 g/m$^2$ (silver coverage) |
| Sensitizing Dye (I) | $6 \times 10^{-5}$ mol per mol of silver |
| Sensitizing Dye (II) | $1.5 \times 10^{-5}$ mol per mol of silver |
| Coupler A | 0.04 mol per mol of silver |
| Coupler C | 0.003 mol per mol of silver |
| Coupler P | 0.0006 mol per mol of silver |

Fourth Layer: Second Red-Sensitive Emulsion Layer (RL$_2$)

| | |
|---|---|
| Silver iodobromide emulsion (silver iodide: 4 mol %) | 1.4 g/m$^2$ (silver coverage) |
| Sensitizing Dye (I) | $3 \times 10^{-5}$ mol per mol of silver |
| Sensitizing Dye (II) | $1.2 \times 10^{-5}$ mol per mol of silver |
| Coupler A | 0.005 mol per mol of silver |
| Coupler C | 0.0016 mol per mol of silver |
| Compound (5) of the Invention (auxiliary developing agent precursor) | 0.0008 mol per mol of silver |

Fifth Layer: Intermediate Layer (ML)
Same as the second layer.
Sixth Layer: First Green-Sensitive Emulsion Layer (GL$_1$)

| | |
|---|---|
| Silver iodobromide emulsion (silver iodide: 4 mol %) | 1.5 g/m$^2$ (silver coverage) |
| Sensitizing Dye (III) | $3 \times 10^{-5}$ mol per mol of silver |
| Sensitizing Dye (IV) | $1 \times 10^{-5}$ mol per mol of silver |
| Coupler B | 0.05 mol per mol of silver |
| Coupler M | 0.008 mol per mol of silver |
| Coupler Q | 0.0015 mol per mol of silver |

Seventh Layer: Second Green-Sensitive Layer (GL$_2$)

| | |
|---|---|
| Silver iodobromide emulsion (silver iodide: 5 mol %) | 1.6 g/m$^2$ (silver coverage) |
| Sensitizing Dye (III) | $2.5 \times 10^{-5}$ mol per mol of silver |
| Sensitizing Dye (IV) | $0.8 \times 10^{-5}$ mol per mol of silver |
| Coupler B | 0.02 mol per mol of silver |

| | |
|---|---|
| Coupler M | 0.003 mol per mol of silver |
| Compound (12) of the Invention (antifoggant precursor) | 0.0002 mol per mol of silver |

Eighth Layer: Yellow Filter Layer (YFL)

A gelatin layer containing a dispersion of yellow colloidal silver and 2,5-di-tert-octylhydroquinone in an aqueous gelatin solution.

Ninth Layer: First Blue-Sensitive Emulsion Layer (BL$_1$)

| | |
|---|---|
| Silver iodobromide emulsion (silver iodide: 6 mol %) | 1.5 g/m$^2$ (silver coverage) |
| Coupler Y | 0.25 mol per mol of silver |

Tenth Layer: Second Blue-Sensitive Emulsion Layer (BL$_2$)

| | |
|---|---|
| Silver iodobromide emulsion (silver iodide: 6 mol %) | 1.1 g/m$^2$ (silver coverage) |
| Coupler Y | 0.06 mol per mol of silver |

Eleventh Layer: Protective Layer (PL)

Prepared by coating a gelatin layer containing polymethyl methacrylate grains (diameter: about 1.5μ).

In addition to the composition as described above, a gelatin hardener and a surfactant were added to each layer.

Sensitizing Dye (I):
Anhydro-5,5'-dichloro-3,3'-di(γ-sulfopropyl)-9-ethyl-thiacarbocyaninehydroxide pyridinium salt.

Sensitizing Dye (II):
Anhydro-9-ethyl-3,3'-di(γ-sulfopropyl)-4,5,4',5'-dibenzothiacarbocyaninehydroxide triethylamine salt.

Sensitizing Dye (III):
Anhydro-9-ethyl-5,5'-dichloro-3,3'-di(γ-sulfopropyl)oxacarbocyanine sodium salt.

Sensitizing Dye (IV):
Anhydro-5,6,5',6'-tetrachloro-1,1'-diethyl-3,3'-di[β-(γ-sulfopropoxy)ethoxy]ethylimidazolocarbocyanine hydroxide sodium salt.

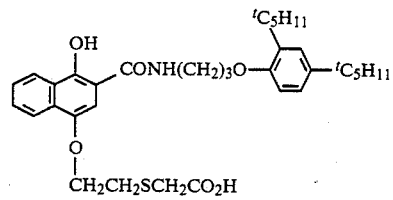

Coupler A:

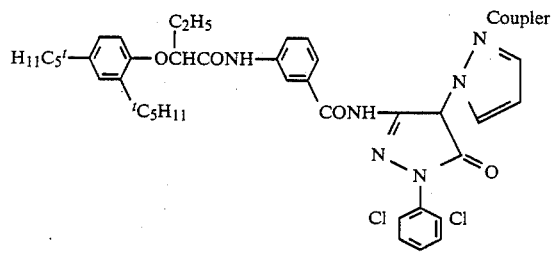

Coupler B

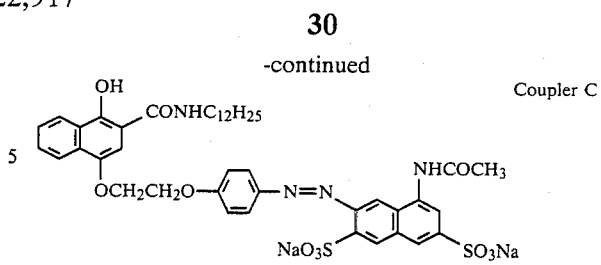

Coupler C

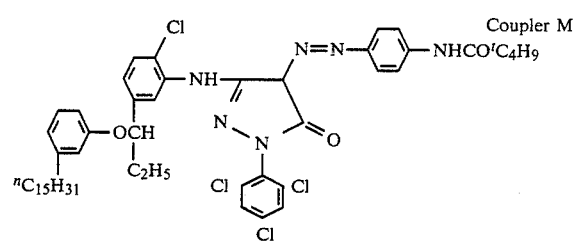

Coupler M

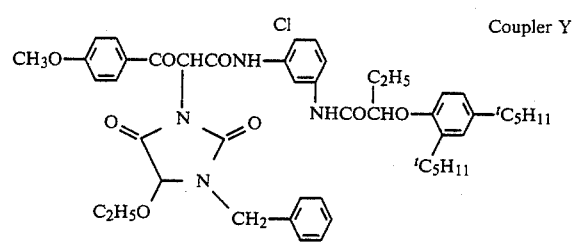

Coupler Y

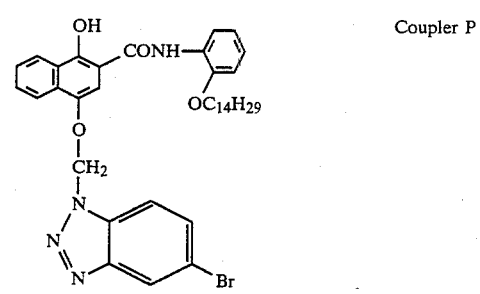

Coupler P

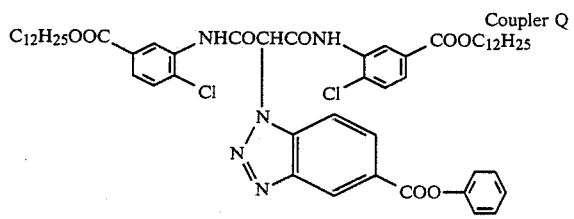

Coupler Q

The material thus prepared was fabricated in a 35 mm size film and exposed imagewise to light. Then, the development as described below was conducted in a 2-liter developer tank.

| | |
|---|---|
| 1. Color Development | 3 min. 15 sec. |
| 2. Bleaching | 6 min. 30 sec. |
| 3. Water Washing | 3 min. 15 sec. |
| 4. Fixing | 6 min. 30 sec. |
| 5. Water Washing | 3 min. 15 sec. |
| 6. Stabilization | 3 min. 15 sec. |

The composition of the processing solution at each step is as follows:

| Color Developer | |
|---|---|
| Sodium nitrilotriacetate | 1.0 g |
| Sodium sulfite | 4.0 g |

| | |
|---|---|
| Sodium carbonate | 30.0 g |
| Potassium bromide | 1.4 g |
| Hydroxylamine sulfate | 2.4 g |
| 4-(N—Ethyl-N—β-hydroxyethylamino)-2-methylaniline sulfate | 4.5 g |
| Water to make | 1,000 ml |
| Bleaching Solution | |
| Ammonium bromide | 160.0 g |
| Ammonia water (28%) | 25.0 ml |
| Iron sodium ethylenediaminetetra-acetate | 130 g |
| Glacial acetic acid | 14 ml |
| Water to make | 1,000 ml |
| Fixing Solution | |
| Sodium tetrapolyphosphate | 2.0 g |
| Sodium sulfite | 4.0 g |
| Ammonium thiosulfate (70%) | 175.0 ml |
| Sodium bisulfite | 4.6 g |
| Water to make | 1,000 ml |
| Stabilizing Solution | |
| Formalin | 8.0 ml |
| Water to make | 1,000 ml |

The multilayer color light-sensitive material as prepared above produced a sharp negative color image.

While the invention has been described in detail and with reference to specific embodiments thereof, it will be apparent to one skilled in the art that various changes and modifications can be made therein without departing from the spirit and scope thereof.

What is claimed is:

1. A photographic silver halide light-sensitive material, comprising:
a support base having thereon:
a silver halide emulsion layer and another layer; wherein at least one of said layers contains a compound represented by the general formula (I):

$$A\text{—}OCH_2\text{—}Z \qquad (I)$$

wherein A represents a group capable of undergoing cleavage on application of alkali hydrolysis and represents a group selected from the following:

$$R_1\text{—}\underset{\underset{O}{\|}}{C}\text{—}$$

$$R_1O\text{—}\underset{\underset{O}{\|}}{C}\text{—}$$

$$\underset{R_3}{\overset{R_2}{\diagdown}}N\text{—}\underset{\underset{O}{\|}}{C}\text{—}$$

$$R_1S\text{—}\underset{\underset{O}{\|}}{C}\text{—}$$

$$R_1\text{—}\underset{\underset{O}{\|}}{C}\text{—}\underset{\underset{O}{\|}}{C}\text{—}$$

$$\underset{R_3}{\overset{R_2}{\diagdown}}N\text{—}\underset{\underset{\underset{R_1}{|}}{N}}{\overset{\|}{C}}\text{—}$$

$$R_1\text{—}\underset{\underset{\underset{R_2}{|}}{N}}{\overset{\|}{C}}\text{—}$$

and $$R_1O\text{—}\underset{\underset{\underset{R_2}{|}}{N}}{\overset{\|}{C}}\text{—}$$

wherein $R_1$ is an aliphatic group containing from 1 to 22 carbon atoms, an aromatic group containing from 6 to 10 carbon atoms or a heterocyclic group; and $R_2$ and $R_3$ are each a hydrogen atom, an aliphatic group containing 1 to 22 carbon atoms, an aromatic group containing 6 to 10 atoms, or a heterocyclic group, and $R_2$ and $R_3$ may combine together to form a ring; and wherein Z is a group selected from the following:

(II)

(III)

(IV)

(V)

wherein $R_4$, $R_5$ and $R_6$ independently represent a hydrogen atom, an aliphatic group, or an aromatic group;

$R_7$ represents an amino group, an alkoxyl group, an aryloxy group, a hydroxyl group, an alkyl group, an aryl group, a halogen atom, a carbonamide group, a sulfonamide group, an alkanoyloxy group, a benzoyloxy group, a ureido group, a carbamate group, a carbamoyloxy group, a carbonate group, or a carboxyl group;

$R_8$ may represent the same groups as $R_7$ and, an alkoxycarbonyl group, an aryloxycarbonyl group, a carbamoyl group, a sulfamoyl group, an alkanoyl group, a benzoyl group, an alkylsulfonyl group, an arylsulfonyl group, a cyano group, a sulfo group or a nitro group;

$R_9$ represents an aliphatic group or an aromatic group;

l represents 0 or an integer of from 1 to 5; and m is 0 or an integer of from 1 to 4.

2. A photographic silver halide light-sensitive material as claimed in claim 1, wherein A represents a group selected from the following:

and

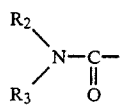

wherein $R_1$ is an aliphatic group containing from 1 to 22 carbon atoms, an aromatic group containing from 6 to 10 carbon atoms or a heterocyclic group; and $R_2$ and $R_3$ are each a hydrogen atom, an aliphatic group containing 1 to 22 carbon atoms, an aromatic group containing 6 to 10 carbon atoms, or a heterocyclic group, and $R_2$ and $R_3$ may combine together to form a ring.

3. A photographic silver halide light-sensitive material as claimed in claim 1, wherein the compound represented by the general formula (I) is an auxiliary developing agent precursor.

4. A photographic silver halide light-sensitive material as claimed in claim 1, wherein the compound represented by the general formula (I) is a development inhibitor precursor.

5. A photographic silver halide light-sensitive material as claimed in claim 1, wherein the compound represented by the general formula (I) is a silver halide solvent precursor.

6. A photographic silver halide light-sensitive material as claimed in claim 1, wherein the compound represented by the general formula (I) is an antifoggant precursor.

7. A photographic silver halide light-sensitive material as claimed in claim 1, wherein the compound represented by the general formula (I) is present in a silver halide emulsion layer or its adjacent layer.

8. A photographic silver halide light-sensitive material as claimed in claim 1, wherein an amount of the compound represented by the general formula (I) is from $1 \times 10^{-7}$ to $1 \times 10^{-1}$ mol per mol of silver.

9. A photographic silver halide light-sensitive material as claimed in claim 1, wherein A represents

10. A photographic silver halide light-sensitive material as claimed in claim 1, wherein A represents

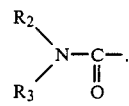

11. A photographic silver halide light-sensitive material as claimed in claim 1, wherein A represents

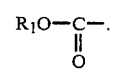

12. A photographic silver halide light-sensitive material as claimed in claim 1, wherein A represents

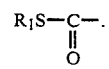

13. A photographic silver halide light-sensitive material as claimed in claim 1, wherein A represents

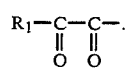

14. A photographic silver halide light-sensitive material as claimed in claim 1, wherein A represents

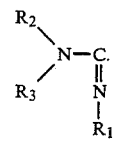

15. A photographic silver halide light-sensitive material as claimed in claim 1, wherein A represents

16. A photographic silver halide light-sensitive material as claimed in claim 1, wherein A represents

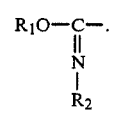

* * * * *